(12) United States Patent
Butler et al.

(10) Patent No.: US 9,072,549 B2
(45) Date of Patent: Jul. 7, 2015

(54) SPINAL CLIPS FOR INTERSPINOUS DECOMPRESSION

(75) Inventors: Michael S. Butler, St. Charles, IL (US); Daniel Predick, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 295 days.

(21) Appl. No.: 13/161,916

(22) Filed: Jun. 16, 2011

(65) Prior Publication Data

US 2011/0313458 A1 Dec. 22, 2011

Related U.S. Application Data

(60) Provisional application No. 61/355,204, filed on Jun. 16, 2010.

(51) Int. Cl.
*A61B 17/70* (2006.01)

(52) U.S. Cl.
CPC .................................. *A61B 17/7065* (2013.01)

(58) Field of Classification Search
CPC ........... A61B 17/7062; A61B 17/7065; A61B 17/7068; A61F 2/4405
USPC .................. 606/248–249, 324–328
See application file for complete search history.

(56) References Cited

U.S. PATENT DOCUMENTS

| | | | |
|---|---|---|---|
| 2006/0293662 A1* | 12/2006 | Boyer et al. | 606/61 |
| 2007/0161992 A1* | 7/2007 | Kwak et al. | 606/61 |
| 2007/0233082 A1* | 10/2007 | Chin et al. | 606/61 |
| 2007/0270840 A1* | 11/2007 | Chin et al. | 606/61 |
| 2010/0241166 A1* | 9/2010 | Dwyer et al. | 606/249 |

* cited by examiner

*Primary Examiner* — Eduardo C Robert
*Assistant Examiner* — Julianna N Harvey
(74) *Attorney, Agent, or Firm* — Foley & Lardner LLP (57) ABSTRACT

A spinal clip for creating a potential space within the spinal canal and thus stabilizing the spine without the need for additional spinal components is embodied in different forms. The spinal clips are configured to provide a clamping or holding force against and/or to the spinous processes, transverse processes and/or the lamina of adjacent vertebrae. In one form, the spinous process clips utilize pivoting to effect clamping or holding. In another form, the spinous process clips utilize rotation to effect clamping or holding. Such rotation may be between clamping or holding members or via a screw system. In yet another form, the spinous process clips utilize ratcheting to effect clamping or holding. In a still further form, the spinous process clips utilize expansion to effect clamping or holding. Depending on the form of clamping or holding, the spinous process clips can provide infinite adjustment of the clamping or holding force within an adjustment range, or provide discrete steps or levels of the clamping or holding force.

22 Claims, 7 Drawing Sheets

Fig. 12

SPINAL CLIPS FOR INTERSPINOUS DECOMPRESSION

RELATED APPLICATIONS

This patent application claims the benefit of and/or priority under 35 U.S.C. §119(e) to U.S. Provisional Patent Application Ser. No. 61/355,204 filed Jun. 16, 2010, entitled "Spinal Clips For Interspinous Decompression" the entire contents of which is specifically incorporated herein by this reference.

BACKGROUND OF THE INVENTION

1. Field of the Invention

The present invention relates to implants for the spine and, more particularly, to spinal implants pertaining to the spinous process of the spine.

2. Background Information

As we age various changes can occur in the body. For instance, the ligaments of the spine can thicken and calcify (i.e. harden from deposits of calcium), bone and joints may enlarge, bone spurs called osteophytes may form, spinal discs may collapse and bulge (i.e. herniate) or one vertebra may slip over another (spondylolisthesis). Any one or these conditions and/or others can cause what is known as spinal stenosis. Spinal stenosis is a narrowing of the bony spinal canal. While some people are born with this condition, most often spinal stenosis is the result of one of the above-identified degenerative conditions that develop in mainly the middle-aged and elderly population.

In this regard, spinal stenosis may be considered as the gradual result of aging and "wear and tear" on the spine from everyday activities. Such degenerative or age-related changes in our bodies can lead to compression of nerves (i.e. pressure on the nerves that can cause pain and/or damage). Symptoms of spinal stenosis include leg pain ("pins and needles") that can limit standing, walking, self-supporting daily activities, work, social and recreational pursuits. Lack of activity because of spinal stenosis may lead to obesity, depression and general physical deterioration.

Once diagnosed with spinal stenosis the doctor will usually try non-surgical treatments first. Such treatments may include anti-inflammatory medications (orally or by injection) to reduce associated swelling or analgesic drugs to control pain. Physical therapy may be prescribed with goals of improving ones strength, endurance and flexibility so that you can maintain or resume a more normal lifestyle. Spinal injections such as an epidural injection of cortisone may also be used. Such non-surgical treatments do not correct the spinal canal narrowing of spinal stenosis itself but may provide long-lasting pain control and improved life function without requiring a more invasive treatment. However, as a last resort for those patients who don't respond to non-surgical treatments, surgery will be advised.

Spinal stenosis is one of the most common reason for back surgery in people over the age of 50 in the United States. While there are various non-surgical treatments for spinal stenosis, a surgical procedure known as a laminectomy may be performed in order to reduce or eliminate the symptoms of spinal stenosis. A laminectomy or spinal decompression surgery has the goal of opening up the bony canal to improve available space for the spinal nerves. As indicated, however, a laminectomy is usually a last resort for treating spinal stenosis. This is because a laminectomy is an invasive surgical procedure. Other invasive spinal decompression surgical procedures include the laminotomy, the foraminotomy and the facetectonomy.

Fortunately, another surgical treatment for spinal stenosis is known that is less invasive than a laminectomy. This other surgical treatment involves implanting a device between bony projections of adjacent vertebrae, particularly, but not necessarily, between spinous processes of the adjacent vertebrae. This achieves interspinous process decompression for alleviating spinal stenosis. However, even these surgical procedures are still invasive as compared to typical minimally invasive surgical procedures.

In view of the foregoing, it is therefore desirable to provide a compact interspinous process spacer for interspinous process decompression. Moreover, it is desirable to provide an interspinous process spacer for use in minimally invasive surgery that can be placed in a collapsed interspinous space and then expanded.

SUMMARY OF THE INVENTION

Spinal clips are provided for creating a potential space within the spinal canal and thus stabilizing the spine without the need for additional spinal instrumentation. The spinal clips are configured for introduction to the spine in a collapsed state then provide a clamping or holding force against and/or to the spinous processes, transverse processes and/or the lamina of adjacent vertebrae (collectively, spinous processes). The spinal clips utilize mechanical torque and/or tension to deploy and effect retention.

In one form, the spinous process clips utilize pivoting to effect deployment and retention. In another form, the spinous process clips utilize rotation to effect deployment and retention. Such rotation may be between clamping or holding members or via a screw system. In yet another form, the spinous process clips utilize ratcheting to effect deployment and retention. In a still further form, the spinous process clips utilize expansion to effect deployment and retention.

Depending on the form of clamping or holding, the spinous process clips can provide infinite adjustment of the clamping or holding force within an adjustment range, or provide discrete steps or levels of the clamping or holding force.

The spinous process clips are made from a biocompatible material such as PEEK (PolyEtherEtherKetone), titanium, stainless steel or the like that will provide flexure given the geometry or configuration of the unitary body thereof.

The present spinous process clips are an improvement over current devices in that the present spinous process clips can be inserted posteriorly, laterally or posteriorlaterally with minimum tissue resection or posterior-laterally with no ligament resection (i.e. the ligament that covers the spinous process). Other advantages are also achieved.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

A discussion of the features, functions and/or configurations of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE INVENTION

Figure 1:
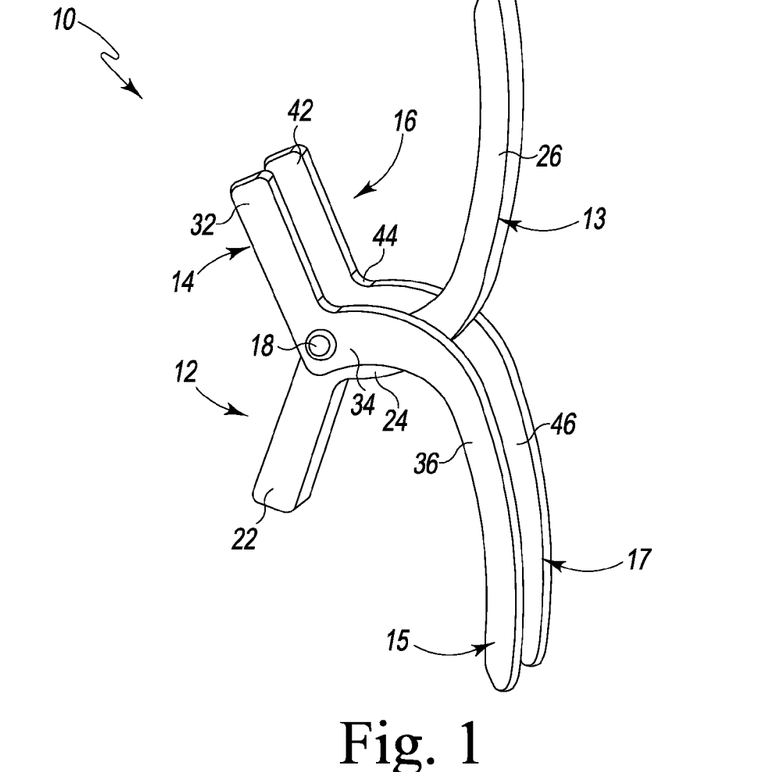
FIG. 1 is a perspective view of an embodiment of a spinous process clip fashioned in accordance with the principles of the present invention, the spinous process clip shown in an open (clamping/holding) position or state.
Figure 2:
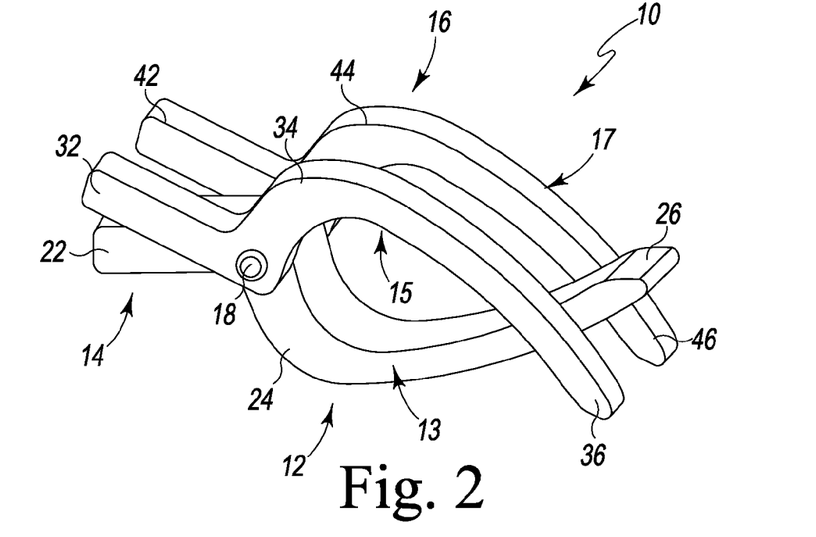
FIG. 2 is a perspective view of the spinous process clip of FIG. 1 shown in a closed (insertion) or unexpanded position or state.

Referring to FIGS. 1-2, there is shown one exemplary embodiment of a spinous process clip generally designated 10 fashioned in accordance with the present principles. The spinous process clip 10, is used for posterior, lateral and/or posterior-lateral insertion into the interspinous process space and thus is configured to retract or be closed prior to and during insertion, then expand or deploy once inserted onto the spine space with minimum tissue resection. The spinous process clip 10 is made from a biocompatible material such as PEEK (polyetheretherketone), titanium or stainless steel. It should be appreciated that other biocompatible materials may be used.

The spinous process clip 10 is characterized by a three-piece construction, namely a middle portion 12, a first lateral portion 14, and a second lateral portion 16. It should be appreciated that the nomenclature first and second is arbitrary. The first lateral portion 14 and the second lateral portion 16 are pivotally connected to the middle portion 12 via a pivot/pivot pin 18. Thus, the first and second lateral portions 14, 16 may be considered to pivot with respect to the middle portion 12 or the middle portion 12 may be considered to pivot with respect to the first and second lateral portions. In either and both cases, the spinous process clip 10 may be pivoted into the position illustrated in FIG. 1 open (clamping) position, the closed (insertion) position illustrated in FIG. 2, and positions in between the positions illustrated in FIGS. 1 and 2.

The middle portion 12 is formed by a unitary body 13 that defines an arm 22 which extends from one end of an elbow 24, and an arm 26 that extends from the other end of the curved elbow 24. The arm 22 is linear as it extends from the elbow 24, while the arm 26 is curvilinear as it extends from the elbow 24. The elbow 24 is likewise curvilinear as it extends from the arm 22. It should be appreciated that the arm 22 may not necessarily be linear. Additionally, the curvatures of the elbow 24 and arm 26 may be different than that shown.

The first lateral portion 14 is formed by a unitary body 15 that defines an arm 32 which extends from one end of an elbow 34, and an arm 36 that extends from the other end of the curved elbow 34. The arm 32 is linear as it extends from the elbow 34, while the arm 36 is curvilinear as it extends from the elbow 24. The elbow 34 is likewise curvilinear as it extends from the arm 32. It should be appreciated that the arm 32 may not necessarily be linear. Additionally, the curvatures of the elbow 34 and arm 36 may be different than that shown.

The second lateral portion 16 is formed by a unitary body 17 defining and arm 42 which extends from one end of an elbow 44, and an arm 46 that extends from the other end of the curved elbow 44. The arm 42 is linear as it extends from the elbow 44, while the arm 46 is curvilinear as it extends from the elbow 44. The elbow 44 is likewise curvilinear as it extends from the arm 42. It should be appreciated that the arm 42 may not necessarily be linear. Additionally, the curvatures of the elbow 44 and arm 46 may be different than that shown.

The first and second lateral portions 14, 16 are situated relative to the middle portion 14 such that the curvatures of the elbows 34, 44 and arms 35, 46 of the first and second lateral portions 14, 16 are opposite the curvature of the elbow 24 and arm 26 of the middle portion. The opposite curvatures of the elbow/arm combinations of the first and second lateral portions 14, 16 relative to the elbow/arm combination of the middle portion 12, define a clamping space between the respective elbow/arm combinations of the first and second lateral portions 14, 16 and the middle portion 12, and thus the ability to clamp onto the spinous processes, transverse processes or the lamina of a vertebra.

The spinous process clip 10 is adjustable and/or provides clamping. Adjustment is effected by the pivoting of the middle and the first and second lateral portions. In order for the spinous process clip 10 to provide clamping and/or a clamping force and/or to maintain the clamping force, a bias is provided between the first and second lateral portions 14, 16 and the middle portion 12. Such bias is provided through the pivot/pivot pin 18. Other manners of providing a clamping force bias between the first and second lateral portions 14, 16 and the middle portion 12 may be used and are contemplated.

Figure 3:
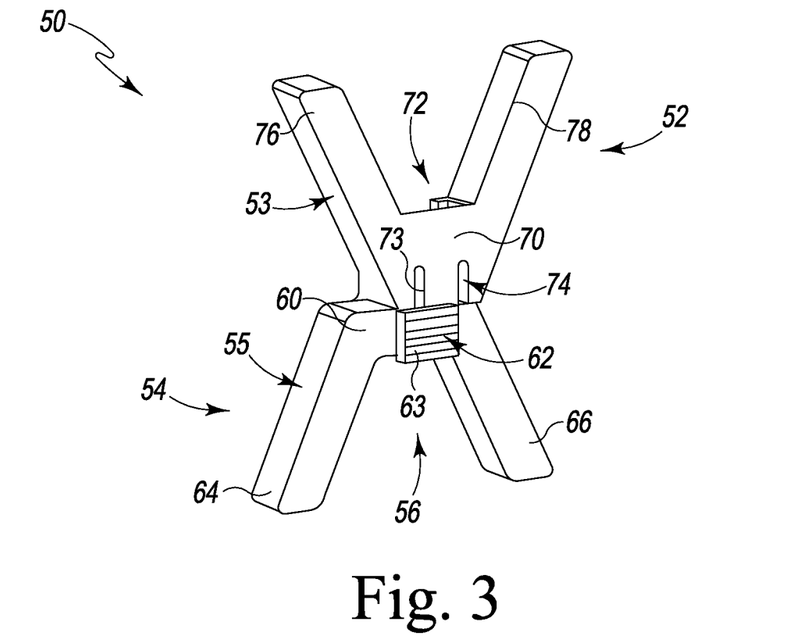
FIG. 3 is a perspective view of another embodiment of a spinous process clip fashioned in accordance with the principles of the present invention, the spinous process clip shown in a holding position or state.
Figure 4:
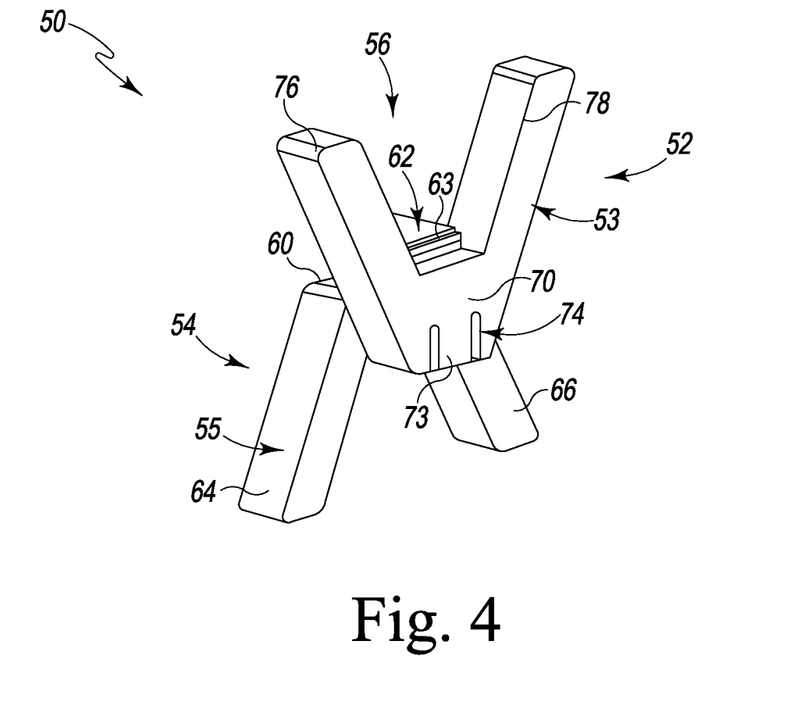
FIG. 4 is a perspective view of the spinous process clip of FIG. 3 shown in an insertion position or state.

Referring now to FIGS. 3-4, there is shown another exemplary embodiment of a spinous process clip generally designated 50 fashioned in accordance with the present principles. Like the spinous process clip 10 the spinous process clip 50 is used for spinal distraction and stabilization and thus is configured to compress and expand, and to be inserted posteriorly onto the spine with minimum tissue resection. The spinous process clip 50 is also made from a biocompatible material such as PEEK (polyetheretherketone), titanium or stainless steel. It should be appreciated that other biocompatible materials may be used.

The spinous process clip 50 utilizes a combined gear rack and ratchet mechanism similar in form and function to that of a zip strip (cable tie) in order to effect adjustment thereof. The spinous process clip 50 is characterized by a two-piece construction, namely a first or upper portion 52, and a second or lower portion 54. It should be understood that the nomenclature upper, lower, first and second are arbitrary. The first portion 52 and the second portion 54 are adjustably connected to each other via a combined gear rack and ratchet mechanism 56. The first and second portions 52, 54 thus move with respect to each other but in discrete steps according to the spacing/geometry of the combined gear rack and ratchet mechanism 56. This is described further below. Movement of the first and second portions 52, 54 allows the spinous process clip 50 to assume the holding position illustrated in FIG. 3, the closed or insertion position illustrated in FIG. 4, and positions in between the positions illustrated in FIGS. 3 and 4.

The first portion 52 is formed by a unitary body 53 that defines a base 70, a first arm 76 which extends from one side of the base 70, and a second arm 78 that extends from the other side of the base 70. Again, it should be appreciated that the nomenclature first and second is arbitrary. The first arm 76 is linear but extends at an angle laterally outwardly from the base 70. The second arm 78 is likewise linear but extends at an angle laterally outwardly from the base 70. The angles of the first and second arms 76, 78 are opposite one another such that the body 53 essentially defines a "V" shape.

The second portion 54 is formed by a unitary body 55 that defines a base 60, a first arm 64 which extends from one side of the base 60, and a second arm 66 that extends from the other side of the base 60. Again, it should be appreciated that the nomenclature first and second is arbitrary. The first arm 64 is linear but extends at an angle laterally outwardly from the base 60. The second arm 66 is likewise linear but extends at an angle laterally outwardly from the base 60. The angles of the first and second arms 64, 66 are opposite one another such that the body 55 essentially defines a "V" shape.

The first and second portions 52, 54 are connected together via the combined gear rack and ratchet 56 such that their respective "V" shapes are opposite or upside down relative to one another. The opposite "V" shapes of the arms of the first and second portions 52, 54 define a clamping or holding space between their respective arms and thus the ability to clamp or hold onto adjacent spinous processes, transverse processes or the lamina (spinal structures) of adjacent vertebrae, as well as fit between the area or space between the adjacent spinal structures.

As indicated above, discrete adjustable movement between the first and second portions 52, 54 is accomplished by the combined gear rack and ratchet 56. Particularly, the first portion 52 includes a gear rack 62 on a side surface of the base 60. The gear rack 62 extends from a top to bottom end of the base 60 and includes a plurality of teeth, serrations or the like 63. The second portion 54 includes a configured slot, channel, groove or the like 72 ("slot") formed in the base 70. The configured slot 72 extends from a top to bottom end of the base 70. The base 70 further includes a flange 73 formed at the end of the configured slot 72. The flange 73 has a pawl or similar protrusion such that the configured slot 72 and flange 73 form the ratchet. Together, the configured slot 72 and the ratchet 62 form the combined gear rack and ratchet 56. The combined gear rack and ratchet 56 allows the first and second portions 52, 54 to discretely move away from each other while preventing backwards movement. For example, if the first portion 52 is moved from the position shown in FIG. 4 to the position shown in FIG. 3, the first portion 52 is prevented from returning to the position shown in FIG. 4. It should be appreciated that while the gear rack is shown as being a part of the first portion 52 and the ratchet is shown as being part of the second portion 54, they can be reversed such that the gear rack may be a part of the second portion and the ratchet may be a part of the first portion.

Figure 5:
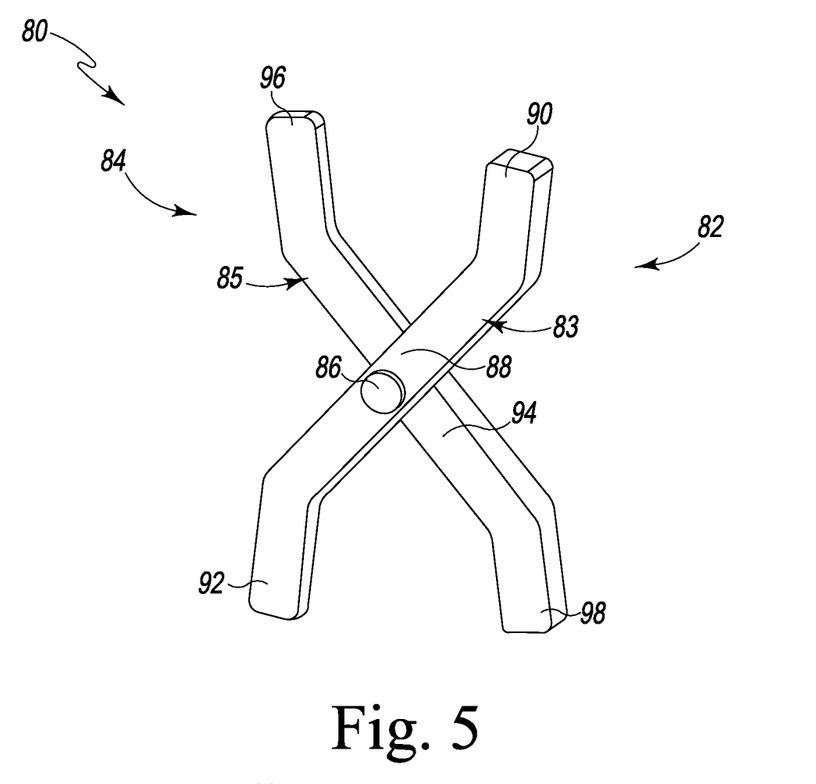
FIG. 5 is a perspective view of another embodiment of a spinous process clip fashioned in accordance with the principles of the present invention, the spinous process clip shown in holding position or state.
Figure 6:
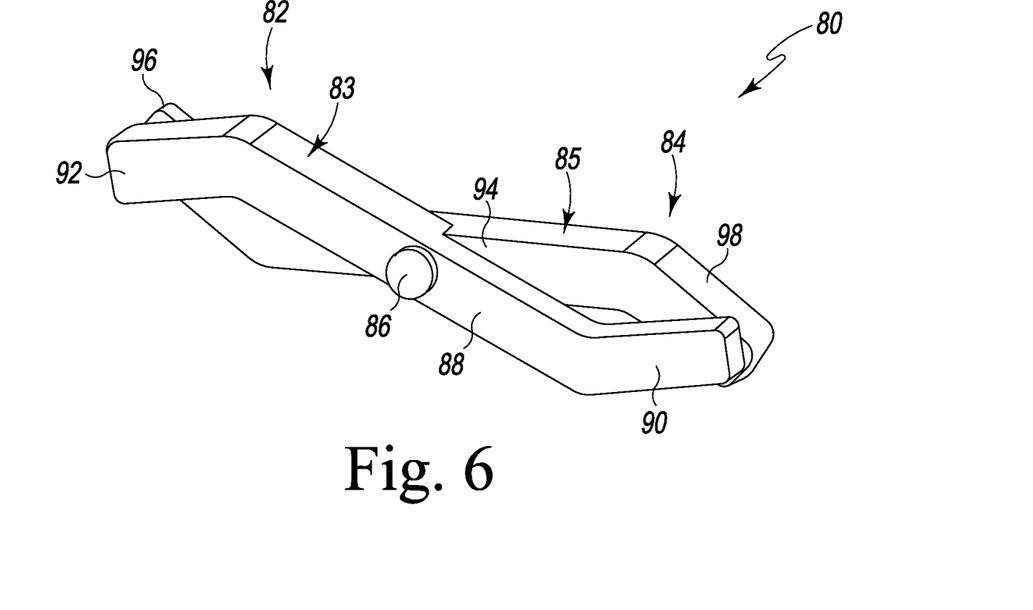
FIG. 6 is a perspective view of the spinous process clip of FIG. 5 shown in a closed (insertion) position or state.

Referring now to FIGS. 5-6, there is shown another exemplary embodiment of a spinous process clip generally designated 80 fashioned in accordance with the present principles. The spinous process clip 80 is used for distraction and stabilization and thus is configured to retract and expand and to be inserted laterally, posterior-laterally or posteriorly onto the spine with no ligament (i.e. the ligament that covers the spinous process) resection. The spinous process clip 80 is made from a biocompatible material such as PEEK (polyetheretherketone), titanium or stainless steel. It should be appreciated that other biocompatible materials may be used.

The spinous process clip 80 is characterized by a two-piece construction, namely a first portion 82, and a second portion 84. It should be appreciated that the nomenclature first and second is arbitrary. The first portion 82 and the second portion 84 are pivotally connected to each other via a pivot/pivot pin 86. Thus, the first and second portions 82, 84 pivot with respect each other. As such, the spinous process clip 80 may be pivoted into the position illustrated in FIG. 5 (an open/holding position), the position illustrated in FIG. 6 (a closed/insertion position), and positions in between the open and closed positions illustrated in FIGS. 5 and 6.

The first portion 82 is formed by a unitary body 83 that defines a middle linear portion 88, a first linear arm 90 extending from an end of the middle linear portion 88, and a second linear arm 92 extending from the other end of the middle linear portion 88. The first linear arm 90 extends at an angle relative to the longitudinal axis of the middle linear portion 88. The second linear arm 92 likewise extends at an angle relative to the longitudinal axis of the middle linear portion 88. The first and second arms 90, 92 extend at opposite angles relative to one another so as to form one "leg" of the "X" shape of the spinous process clip 80.

The second portion 84 is formed by a unitary body 85 that defines a middle linear portion 94, a first linear arm 96 extending from an end of the middle linear portion 94, and a second linear arm 98 extending from the other end of the middle linear portion 94. The first linear arm 96 extends at an angle relative to the longitudinal axis of the middle linear portion 94. The second linear arm 98 likewise extends at an angle relative to the longitudinal axis of the middle linear portion 94. The first and second arms 94, 96 extend at opposite angles relative to one another so as to form the other "leg" of the "X" shape of the spinous process clip 80.

The first and second portions 82, 84 are pivotally coupled to one another such that the arms 90, 96 of the first and second portions 82, 84 extend in the same direction while the arms 92, 98 of the first and second portions 82, 84 extend in the same direction. Thus, when the first and second portions 82, 84 are pivoted into the position shown in FIG. 6 (and other positions from the position shown in FIG. 5) a clamping space is defined between the respective arms of the first and second portions 82, 84, and thus the ability to clamp onto the spinous processes, transverse processes or the lamina of adjacent vertebrae.

The spinous process clip 80 is adjustable and/or provides clamping. Adjustment is effected by the pivoting of the first and second portions. In order for the spinous process clip 80 to provide clamping and/or a clamping force and/or to maintain the clamping force, a bias is provided between the first and second lateral portions 82, 84. Such bias is provided through the pivot/pivot pin 86. Other manners of providing a clamping force bias between the first and second lateral portions 82, 84 may be used and are contemplated.

Figure 7:
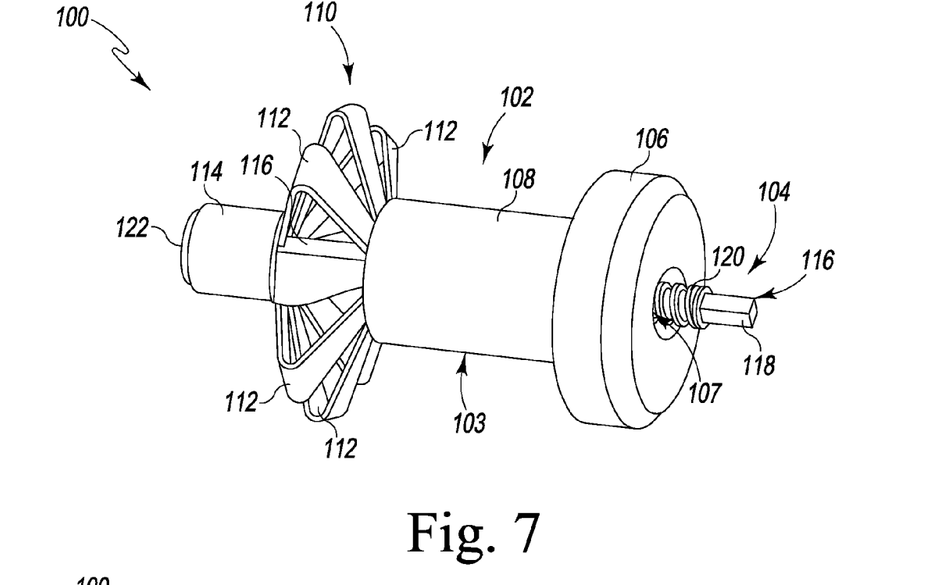
FIG. 7 is a perspective view of another embodiment of a spinous process clip fashioned in accordance with the principles of the present invention, the spinous process clip shown in an expanded (holding) position or state.
Figure 8:
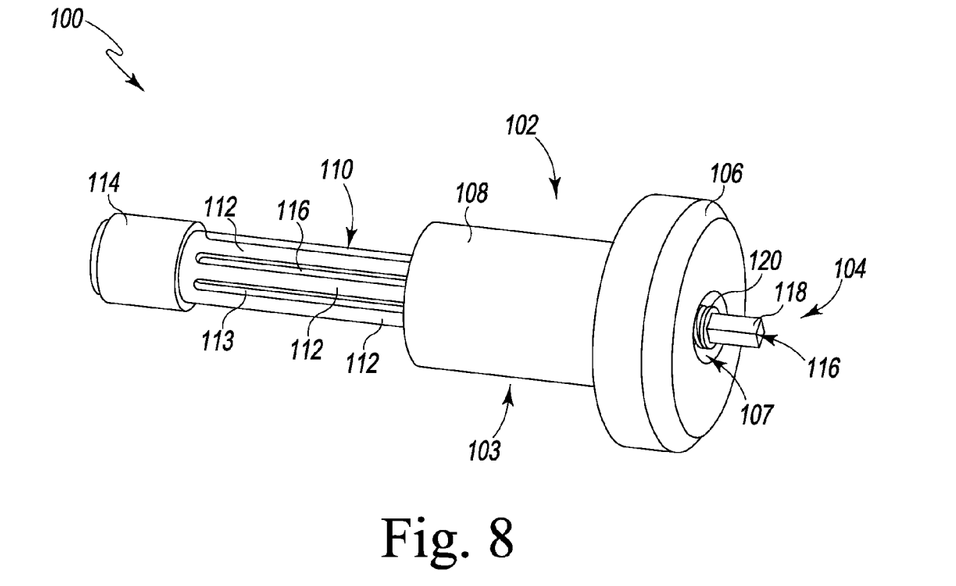
FIG. 8 is a perspective view of the spinous process clip of FIG. 7 shown in an unexpanded (insertion) position or state.

Referring now to FIGS. 7-8, there is shown another exemplary embodiment of a spinous process clip generally designated 100 fashioned in accordance with the present principles. The spinous process clip 100 is used for distraction and stabilization of adjacent vertebrae and thus is configured to be inserted laterally, posterolaterally, and posteriorly onto the spine with minimum tissue resection. The spinous process clip 100 is made from a biocompatible material such as PEEK (polyetheretherketone), titanium or stainless steel. It should be appreciated that other biocompatible materials may be used.

The spinous process clip 100 is characterized by a two-piece construction, namely a bolt 102 and an expander 104. The bolt 102 is formed by a unitary body 103 that defines a generally cylindrical head 106 with an elongated cylindrical portion 108 extending from one side of the cylindrical head 106. The bolt body 103 further defines an expansion portion 110 that extends axially from the elongated cylindrical portion 108. The expansion portion 110 is formed by a plurality of elongated axial slats 112 that define a plurality of elongated axial openings 113 and terminates in a cylindrical end 114. The plurality of elongated axial slats 112 thus extend from the elongated cylindrical portion 108 to the cylindrical end 114.

The expander 104 is characterized by a shaft 116 that extends through a threaded bore 107 of the cylindrical head 106 of the bolt body 103, a bore of the bolt body 103, the expansion portion 110, a bore of the cylindrical end 114, and terminates in a plate 122 at the axial end of the cylindrical end 114. The shaft 116 has a hexagonal head 118 proximate the cylindrical head 106 that receives a tool for rotating the shaft 116. It should be appreciated that the head 118 of the shaft 116 may take other shapes as desired. The shaft 116 further has a threaded portion 120 that operatively engages the threaded bore 120 of the cylindrical head 106.

The spinous process clip 100 is implanted in an unexpanded position such as illustrated in FIG. 8. Rotation of the shaft 116 pulls the plate 122 against the cylindrical end 114. Compression of the plate 122 against the cylindrical end 114 causes the slats 112 to fold or buckle into an expanded position such as is illustrated in FIG. 7. The provides the ability of the spinous process clip 100 to clamp onto the spinous processes, transverse processes or the lamina of adjacent vertebrae. Particularly, the spinous process clip 100 provides clamping between the cylindrical head 106 and the expanded expansion portion 110.

Figure 9:
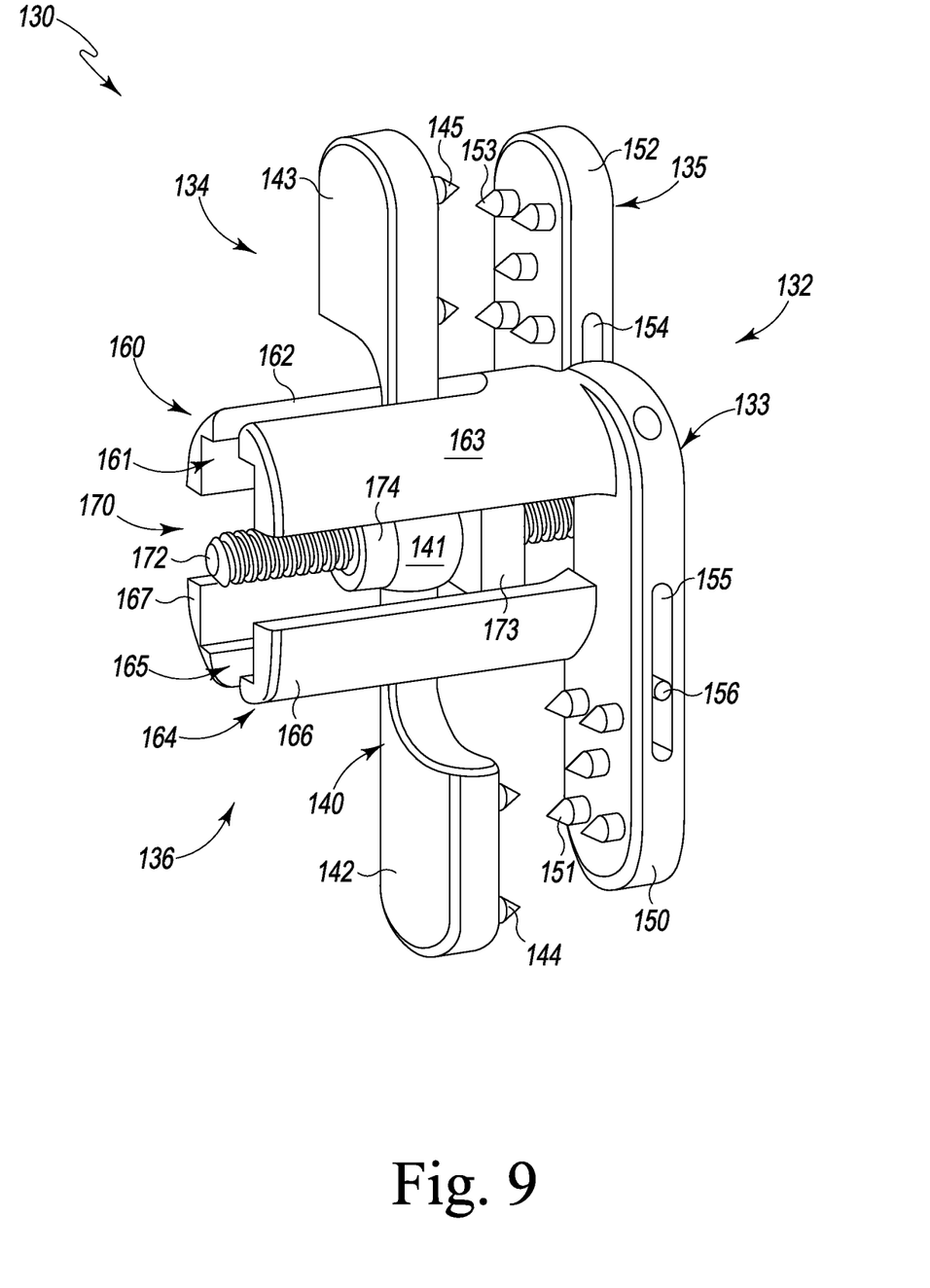
FIG. 9 is a perspective view of another embodiment of a spinous process clip fashioned in accordance with the principles of the present invention, the spinous process clip shown in a clamping position or state.
Figure 10:
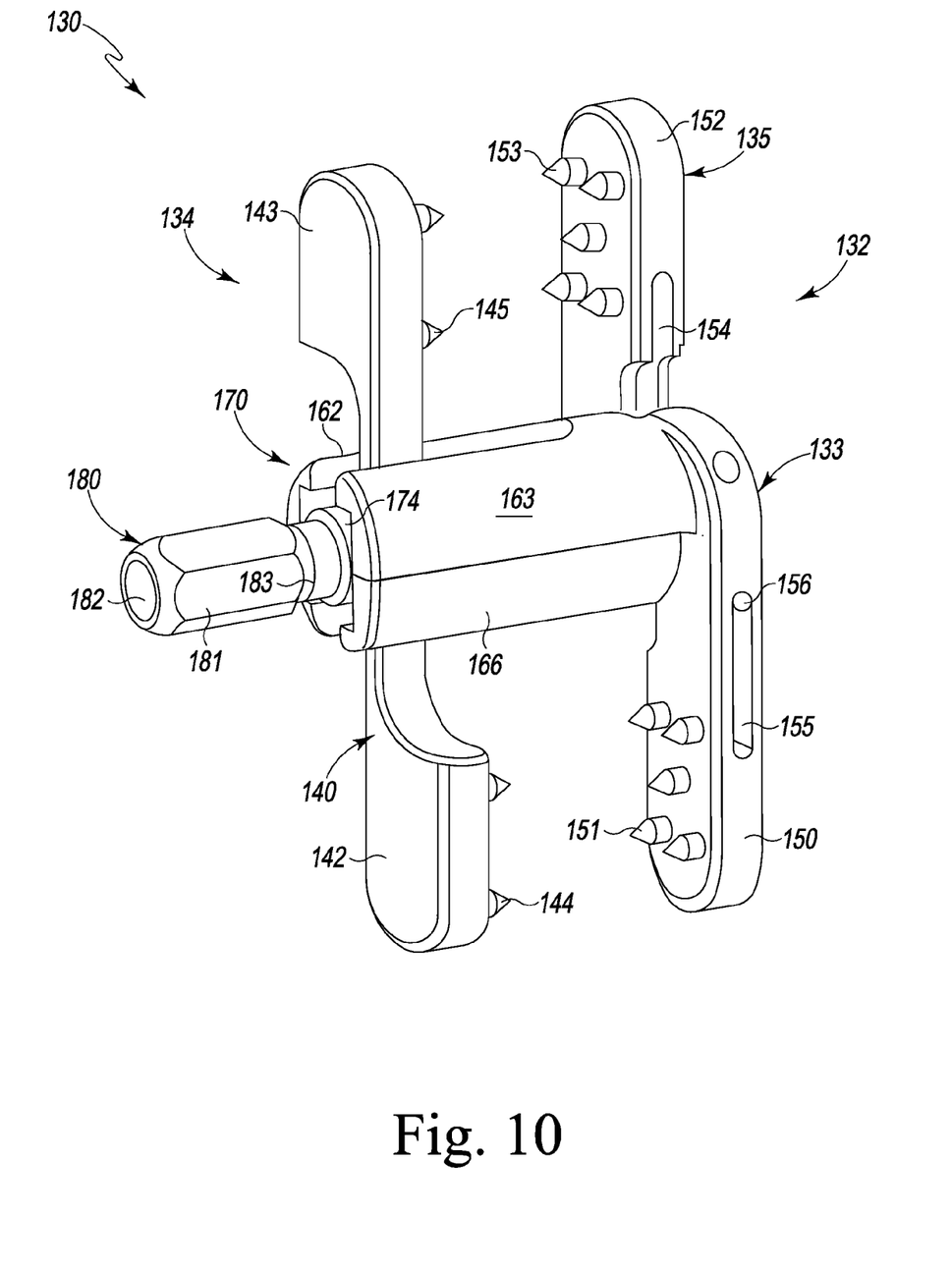
FIG. 10 is a perspective view of the spinous process clip of FIG. 9 shown in an open position or state.

Referring now to FIGS. 9-10, there is shown another exemplary embodiment of a spinous process clip generally designated 130 fashioned in accordance with the present principles. The spinous process clip 130 is used for vertebral expansion and thus is configured to distract and stabilize adjacent vertebrae and to be inserted posteriorly and posterior-laterally onto the spine with no ligament (i.e. the ligament that covers the spinous process) resection. The spinous process clip 130 is made from a biocompatible material such as PEEK (polyetheretherketone), titanium or stainless steel. It should be appreciated that other biocompatible materials may be used.

The spinous process clip 130 is characterized by a multiple construction, namely a first portion 132, a second portion 134, and an adjustment portion 136. It should be appreciated that the nomenclature first and second is arbitrary. The first portion 132 and the second portion 134 are movably connected to each other via a mutual slot and pin configuration whose movement is controlled via the adjustment portion 136. Thus, the first and second portions 132, 134 slide with respect to each other under the control of the adjustment portion 136. As such, the spinous process clip 130 may be adjusted into the position illustrated in FIG. 9 (a clamping position), the position illustrated in FIG. 10 (an open position), and positions in between the open and clamping positions illustrated in FIGS. 10 and 9.

The first portion 132 is formed by a first unitary body 133 that defines a generally elongated oval wing 150 having a generally half-tubular arm 160 extending transverse from an inner surface of an upper portion of the wing 150. The wing 150 also includes a plurality of spikes 151 that project from the inner surface of a lower portion of the wing 150. The spikes 151 are adapted to extend into and grip the spinous processes, transverse processes or the lamina. The arm 160 has a slot 161 that extends through approximately three-quarters (¾) of the length of the arm 160 to essentially divide the arm 160 into a first quarter (¼) 162 and a second quarter (¼) 163. The inside of the first and second quarters 162, 163 are configured to define an upper portion of a rectangular channel.

The first portion 132 is further formed by a second unitary body 135 that defines generally elongated oval wing 152 having a generally half-tubular arm 164 extending transverse from an inner surface of a lower portion of the wing 152. The wing 152 also includes a plurality of spikes 153 that project from the inner surface of an upper portion of the wing 152. The spikes 153 are adapted to extend into and grip the spinous processes, transverse processes or the lamina. The arm 164 has a slot 165 that extends through approximately three-quarters (¾) of the length of the arm 164 to essentially divide the arm 164 into a first quarter (¼) 166 and a second quarter (¼) 167. The inside of the first and second quarters 166, 167 are configured to define an upper portion of a rectangular channel.

The first and second unitary bodies 132, 134 are movably coupled to one another via the mutual slot and pin configuration mentioned above. Particularly, the wing 150 has an elongated slot 155 that extends laterally through the wing 150 from one lateral side thereof to the other. Likewise, the wing 152 has an elongated slot 154 that extends laterally through the wing 152 from one lateral side thereof to the other. The wing 152 has a projection 156 that extends from a lateral side of the wing 152 and into the slot 155 of the wing 150. Likewise, the wing 150 has a projection (not seen) that extends from a lateral side of the wing 150 and into the slot 154 of the wing 150. In this manner, the wings 150, 152 are movably linked to one another.

The second portion 134 is formed of a unitary body 140 that defines an essentially two-ended paddle. The unitary body 140 has a first paddle 142 and a second paddle 143 situated on opposite ends of a mid section. The first paddle 142 has a plurality of spikes 144 on an inside surface thereof that are adapted to extend into and grip the spinous processes, transverse processes or the lamina. The second paddle 143 has a plurality of spikes 145 that are adapted to extend into and grip the spinous processes, transverse processes or the lamina. The mid section has a boss 141 having a bore therethrough.

The adjustment portion 136 includes a central screw 170 that extends through the half tubular arms 160, 164. The screw 170 also extends through a support 173. Support 173 doubly acts as a "shim" used to expand the assembly. A threaded collar 174 is received onto the screw 170 for pushing the second portion 134 towards the first portion 132 and into a clamping or holding position. Initially, the spinous process clip 130 is in the open position as shown in FIG. 10. In order to effect clamping or holding, a drive nut 180 is threaded onto the screw 170. The collar 174 is proximate the second portion 134. The drive nut 180 has a hexagonal body 181 (other shapes may be used) that accepts a hexagonal (or other) driver (not shown). The body 181 has a threaded bore 182 that extends therethrough for receipt onto the screw 170. The body 181 further has an end 183 that is configured to abut the collar 174. Rotation of the drive nut 180 pushes against the collar 174 which pushes against the boss 141 of the second portion 134 to drive the second portion towards the first portion 132. As it does, the wings 150, 154 slide to open the tubular arms 160, 164. At the same time, the second portion 134 moves toward the wings 150, 154 to provide a clamping space therebetween and to provide the ability to clamp onto the spinous processes, transverse processes or the lamina.

Figure 11:
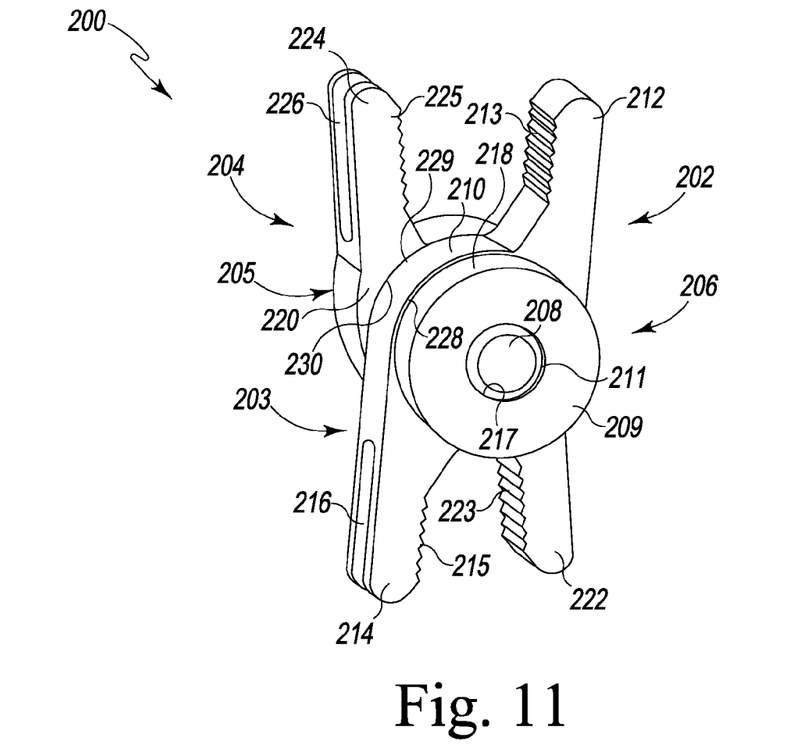
FIG. 11 is a perspective view of another embodiment of a spinous process clip fashioned in accordance with the principles of the present invention, the spinous process clip shown in a clamping position or state.
Figure 12:
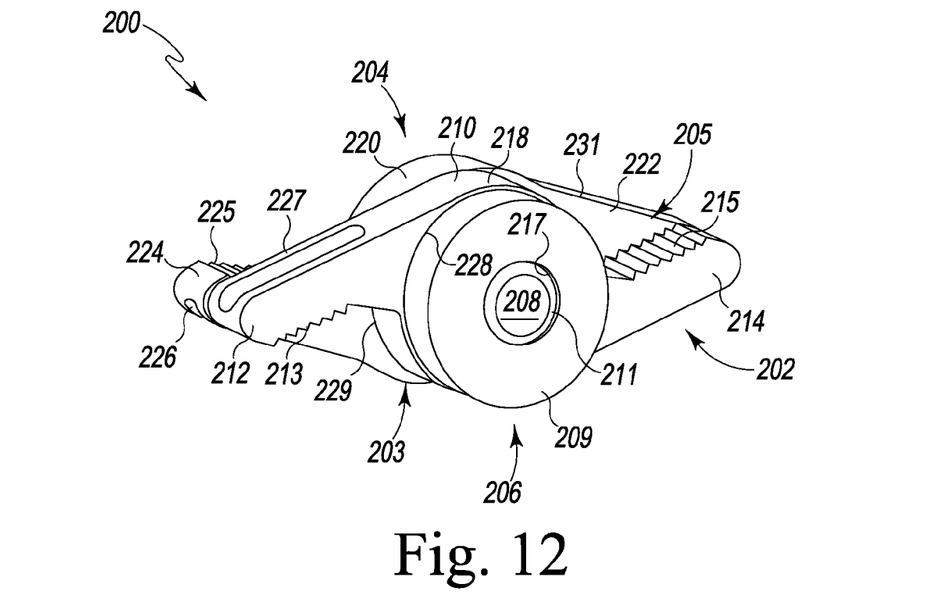
FIG. 12 is a perspective view of the spinous process clip of FIG. 11 shown in a closed position or state.

Referring now to FIGS. 11-12, there is shown another exemplary embodiment of a spinous process clip generally designated 200 fashioned in accordance with the present principles. The spinous process clip 200 is used for distraction and stabilization of the spine and thus is configured to contract and expand and to be inserted laterally, posterior-laterally and posteriorly onto the spine with no ligament (i.e. the ligament that covers the spinous process) resection. The spinous process clip 200 is made from a biocompatible material such as PEEK (polyetheretherketone), titanium or stainless steel. It should be appreciated that other biocompatible materials may be used.

The spinous process clip 200 is characterized by a three-piece construction, namely a first portion 202, a second portion 204, and an adjustment portion 206. It should be appreciated that the nomenclature first and second is arbitrary.

The first portion 202 is formed by a unitary body 203 that defines a central, generally annular hub 210, a first arm 212 extending from a side of the central, generally annular hub 210, and a second arm 214 extending from another side of the central annular hub 210 diametrically opposite the first arm 212. The first arm 212 has a plurality of serrations or teeth 213 on an inside surface thereof (see particularly, FIG. 11) and a longitudinal groove or channel 227 on an outside surface thereof (see particularly, FIG. 12). The second arm 214 has a plurality of serrations or teeth 215 on an inside surface thereof (see particularly, FIG. 12) and a longitudinal groove or channel 216 on an outside surface thereof (see particularly, FIG. 11). The first arm 212 forms one leg of a first clamp of the spinous process clip 200, while the second arm 214 forms one leg of a second clamp of the spinous process clip 200.

The second portion 204 is formed by a unitary body 205 that defines a central, generally annular hub 220, a first arm 222 extending from a side of the central, generally annular hub 220, and a second arm 224 extending from another side of the central annular hub 220 diametrically opposite the first arm 222. The first arm 222 has a plurality of serrations or teeth 223 on an inside surface thereof (see particularly, FIG. 11) and a longitudinal groove or channel 227 on an outside surface thereof (see particularly, FIG. 12). The second arm 224 has a plurality of serrations or teeth 225 on an inside surface thereof (see particularly, FIG. 12) and a longitudinal groove or channel 226 on an outside surface thereof (see particularly, FIG. 11). The first arm 222 forms the other leg of the first clamp of the spinous process clip 200, while the second arm 224 forms the other leg of the second clamp of the spinous process clip 200.

The first portion 202 and the second portion 204 are pivotally or rotatably connected to each other via a pivot/pivot boss 206. Thus, the first and second portions 202, 204 pivot or rotate with respect each other. This can be considered as one portion (either the first or second portion) pivoting or rotating with respect to the other portion (the opposite one of the first and second portion). This allows the spinous process clip 200 to assume the closed position such as is illustrated in FIG. 12 and an open position such as illustrated in FIG. 11. It should be appreciated that the spinous process clip 200 may assume all positions between those shown in the figures.

Moreover, the spinous process clip 200 assumes a plurality of discrete positions each one of which can be locked into place and against further rotation (i.e. positions of the first and second portions 202, 204 are discretely rotatably adjustable relative to one another). This provides clamping by the first clamp, defined by the arms 212 and 224, and by the second clamp, defined by the arms 214 and 222. The discrete positions are provided through meshing of teeth or serrations on the various portions as described below. Particularly, the generally annular hub 220 of the second portion 204 includes a plurality of teeth or serrations 230 situated in a generally annular pattern on an inside surface of the hub 220. Likewise, the generally annular hub 210 of the first portion 202 includes a plurality of teeth or serrations 229 situated in a generally annular pattern on an outside surface of the hub 110. The teeth or serrations 229 rotationally mesh with the teeth or serrations 230 to provide the discrete rotational positions of the first and second portions 202, 204 relative to one another.

In order to lock the positions of the first and second portions 202, 204 relative to one another, the adjustment portion 206 is used. The adjustment portion 206 includes a generally annular knob 209. The knob 209 has a central, threaded bore 217 that is threaded onto the threads 211 of a boss 208 that extends from the hub 220 of the second portion 204 and through the hub 210 of the first portion 202. The knob has a plurality of teeth or serrations 218 situated in a generally annular pattern on an inside surface thereof. The hub 110 of the first portion 202 has a plurality of teeth or serrations 228 situated in a generally annular pattern on an outside surface thereof. The teeth or serrations 218 of the knob 209 rotationally mesh with the teeth or serrations 228 of the hub 110 when the knob 209 rotationally threads onto the threaded boss 208. As the knob 209 is tightened against the hub 210, the teeth 218 of the knob 209 mesh with the outside teeth 228 of the hub 210 which pushes the inside teeth 229 of the hub 210 against the inside teeth 230 of the hub 220 to fix the position of the first and second portions. In this manner, the first and second clamps of the spinous process clip 200 provide the necessary clamping onto the spinous processes, transverse processes or the lamina.

It should be appreciated that variations of the spinous process clip 200 are contemplated but not shown. For example, and without being exhaustive, there may not be threads on elements 208 and 209. The intent of the illustrated spinous process clip 200 is that the knob (209) be compressively held (via tension springs or something of the like) against hubs 210 and 220 to engage the teeth and lock the position. Other manners of accomplishing this may be used.

While the invention has been illustrated and described in detail in the drawings and foregoing description, the same is to be considered as illustrative and not restrictive in character, it being understood that only preferred embodiments have been shown and described and that all changes and/or modifications that come within the spirit of the invention are desired to be protected.

What is claimed is:
1. A spinal implant for posterior, lateral and/or posterior-lateral insertion into an interspinous process space between adjacent vertebrae of a spine in order to stabilize the spine without the need for additional spinal components, the spinal implant comprising:
    a body having a unitary first body portion and a unitary second body portion, one of the first and second body portions pivotable with respect to the other one of the first and second body portions to define a collapsed state and a clamping state; and an adjustment mechanism associated with the first and second body portions and configured to lock the first and second body portions in the collapsed state and in the clamping state providing a first clamp for attachment to a spinous process of a vertebra and a second clamp for attachment to a spinous process of an adjacent vertebra so as to hold the vertebrae in a fixed relationship with each other once clamped;

wherein pivotal movement of the first body portion relative to the second body portion causes a change in clamping size capacity of each of the first clamp and the second clamp;

wherein the first body portion includes a first central annular hub, a first arm extending from the first central annular hub, and a second arm extending from the first central annular hub opposite the first arm, wherein outer surfaces of the first and second arms extend tangentially from an outer surface of the first central annular hub;

wherein the second body portion includes a second central annular hub pivotally engaging the first central annular hub, a third arm extending from the second central annular hub, and a fourth arm extending from the second central annular hub opposite the third arm, wherein outer surfaces of the third and fourth arms extend tangentially from an outer surface of the second central annular hub; and wherein the first and second arms are disposed to a first side of an interface of the first and second central annular hubs, and wherein the third and fourth arms are disposed to a second side of the interface between the first and second central annular hubs.

2. The spinal implant of claim 1, wherein each of the first, second, third, and fourth arms includes a groove extending along a portion of a length of the arm.

3. The spinal implant of claim 1, wherein the first clamp is defined by a first clamp portion of the first body portion and a first clamp portion of the second body portion, and the second clamp is defined by a second clamp portion of the first body portion and a second clamp portion of the second body portion.

4. The spinal implant of claim 3, wherein the first body portion pivotally engages the second body portion.

5. The spinal implant of claim 4, wherein the first body portion is selectively lockable in a plurality of different positions relative to the second body portion.

6. The spinal implant of claim 3, wherein the first and second clamp portions of the first and second body portions each comprise projections configured to grip a spinous process.

7. The spinal implant of claim 1, wherein the first central annular hub includes a first plurality of teeth and a second plurality of teeth, wherein the first plurality of teeth engage a third plurality of teeth provided on the second central annular hub, and wherein the second plurality of teeth engage a fourth plurality of teeth provided on the adjustment mechanism.

8. A spinal implant comprising:
a unitary first portion comprising a first central hub and a pair of first arms extending in generally opposite directions from the first central hub, wherein each arm of the pair of first arms includes an outer surface extending tangentially from an outer surface of the first central hub;
a unitary second portion comprising a second central hub and a pair of second arms extending in generally opposite directions from the second central hub, wherein each arm of the pair of second arms includes an outer surface extending tangentially from an outer surface of the second central hub wherein an inner face of the first central hub pivotally engages an inner face of the second central hub;
wherein one arm of the pair of first arms and one arm of the pair of second arms defines a first clamp, and wherein another arm of the pair of first arms and another arm of the pair of second arms defines a second clamp.

9. The spinal implant of claim 8, wherein the inner faces of the first and second central hubs comprise teeth configured to mesh together in a plurality of discrete positions.

10. The spinal implant of claim 9, wherein the first and second portions are selectively lockable in each of the plurality of discrete positions.

11. The spinal implant of claim 10, wherein each of the plurality of discrete positions defines a different clamping size for the first and second clamps.

12. The spinal implant of claim 10, further comprising an adjustment member configured to selectively lock the first and second portions relative to each other in each of the plurality of discrete positions.

13. The spinal implant of claim 12, wherein the adjustment member is rotatable to selectively lock the first and second portions relative to each other.

14. The spinal implant of claim 12, further comprising:
a boss extending from the first central hub and through the second central hub and comprising an externally threaded portion;
wherein the adjustment member includes a locking knob comprising an internally threaded portion configured to threadingly engage the externally threaded portion of the boss such that rotation of the locking knob relative to the boss locks the first and second portions relative to each other.

15. The spinal implant of claim 8, wherein the first and second portions pivot about a pivot axis, wherein the arms of the first clamp are offset relative to each other along the pivot axis, and wherein the arms of the second clamp are offset relative to each other along the pivot axis.

16. A spinal implant comprising:
a unitary first member comprising a first central portion, and a first upper arm and a first lower arm both extending from the first central portion, wherein the first upper arm and first lower arm include outer surfaces extending tangentially from an outer surface of the first central portion;
a unitary second member comprising a second central portion configured to pivotally engage the first central portion, the second member further comprising a second upper arm and a second lower arm both extending from the second central portion, wherein the second upper arm and second lower arm include outer surfaces extending tangentially from an outer surface of the second central portion;
an adjustment member rotatably coupled to at least one of the first and second members and configured to enable selective locking of the first member relative to the second member in each of a plurality of positions.

17. The spinal implant of claim 16, wherein the first and second members pivot about a pivot axis, and wherein rotation of the adjustment member about the pivot axis causes the first and second members to move toward each other along the pivot axis.

18. The spinal implant of claim 16, wherein the first and second upper arms define a first clamp configured to engage a first spinous process, and wherein the first and second lower arms define a second clamp configured to engage a second spinous process.

19. The spinal implant of claim 18, wherein each of the plurality of positions defines a different clamping size for the first and second clamps.

20. The spinal implant of claim 16, further comprising:
a boss extending from the first central portion and through the second central portion;
wherein the locking member includes a locking knob configured to threadingly engage the boss.

21. The spinal implant of claim 20, wherein the locking knob and second member each comprise teeth configured to mesh with each other as the locking knob threadingly engages the boss.

22. The spinal implant of claim 21, wherein the first and second members each include teeth configured to mesh with each other as the locking knob threadingly engages the boss.

* * * * *